United States Patent [19]

Lennard

[11] Patent Number: 5,587,122
[45] Date of Patent: Dec. 24, 1996

[54] IN-LINE ANNEALING OF SUTURES

[75] Inventor: David J. Lennard, Flemington, N.J.

[73] Assignee: Ethicon, Inc., Somerville, N.J.

[21] Appl. No.: 386,617

[22] Filed: Feb. 10, 1995

[51] Int. Cl.$^6$ .............................. D01D 5/08; D01D 10/02
[52] U.S. Cl. ................................. 264/178 F; 264/210.5; 264/210.7; 264/210.8; 264/235.6; 264/342 RE
[58] Field of Search ......................... 264/178 F, 210.5, 264/210.7, 210.8, 235.6, 342 RE

[56] References Cited

U.S. PATENT DOCUMENTS

| | | | |
|---|---|---|---|
| 5,217,485 | 6/1993 | Liu et al. | 606/228 |
| 5,269,807 | 12/1993 | Liu | 606/228 |
| 5,294,389 | 3/1994 | Hain et al. | 264/342 RE X |
| 5,294,395 | 3/1994 | Broyer | 264/178 F |

Primary Examiner—Leo B. Tentoni
Attorney, Agent, or Firm—Hal Brent Woodrow

[57] ABSTRACT

We have discovered a process for producing a polypropylene suture including the steps of (a) extruding melted polypropylene resin through an orifice and rapidly quenching the melted polypropylene resin to produce a filament; (b) drawing the filament in the range of from about 5× to about 7.5× to produce a singly drawn filament; (c) drawing the singly drawn filament in the range of form about 1× to about 2.5× in a second heated zone being maintained at a temperature in the range of from about 30° C. to about 160° C., to form a doubly drawn filament; (d) shrinking the doubly drawn filament in the range of from about 0.75 percent to about 0.95 percent, in a second heated zone being maintained at a temperature in the range of from about 100° C. to about 180° C., to form a polypropylene suture.

9 Claims, 1 Drawing Sheet

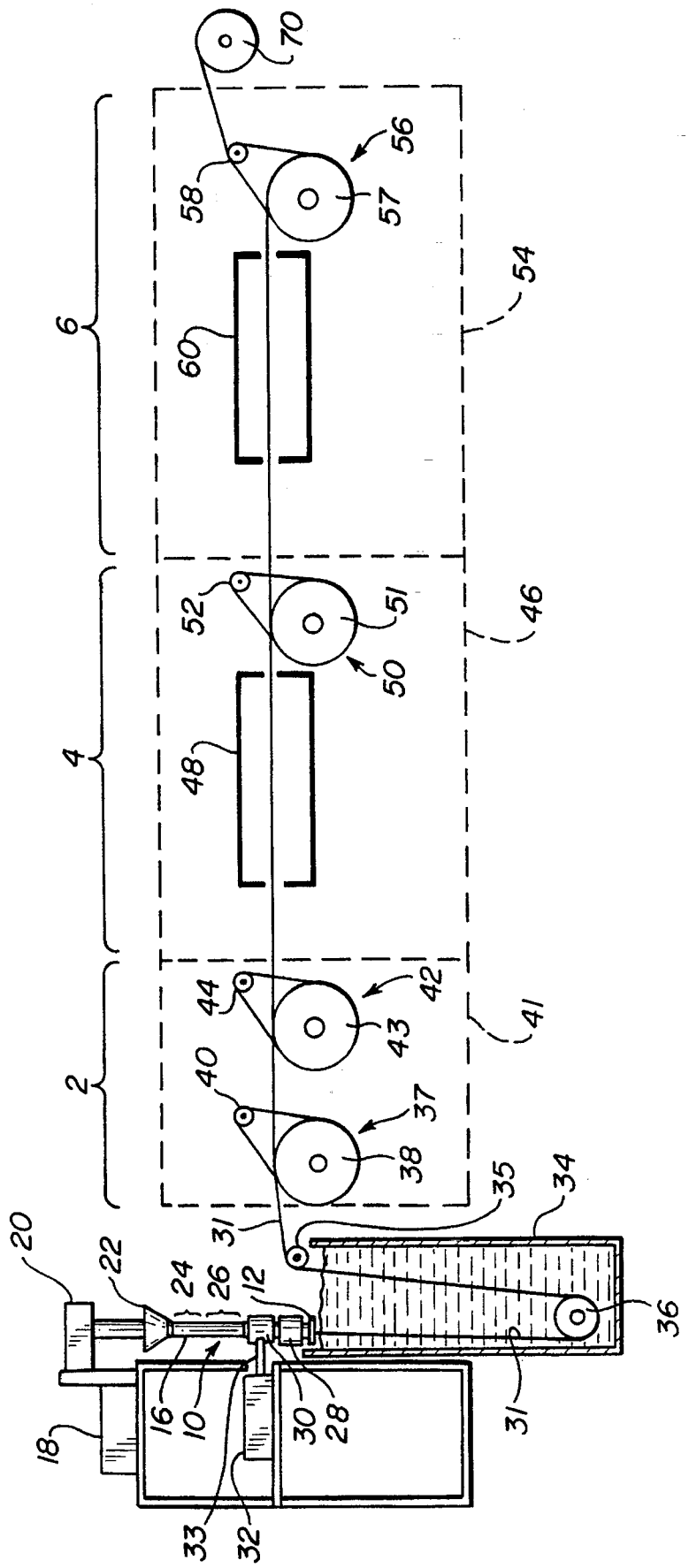

IN-LINE ANNEALING OF SUTURES

FIELD OF THE INVENTION

This invention relates to the field of suture manufacture and more specifically it relates to an in-line process for extruding, drawing and annealing polypropylene sutures.

BACKGROUND OF THE INVENTION

Surgical sutures made from polypropylene have been successfully used by the medical profession for more than twenty years. One of the first commercially successful polypropylene suture to gain wide acceptance was described in U.S. Pat. No. 3,630,205 to Gregory J. Listner. Listner disclosed a process for manufacturing polypropylene suture that comprised the steps of drawing an extruded polypropylene suture to about 6.6 times its original extruded length and then relaxing or shrinking the monofilament to between about 91 to 76 percent of the stretched length.

Lennard et al. in U.S. Pat. No. 4,911,165 later disclosed an improved process for making polypropylene sutures that have increased compliance, limpness or flexibility to make the polypropylene sutures easier to handle and improved their knot security. The process described by Lennard comprised extruding polypropylene through an orifice and quenching the extrudate to form a filament. The filament was first drawn about 6× to 7× then drawn a second time from about 1.06× to about 1.5×. Finally the filament was collected and heat relaxed off-line to effect a linear shrink and heat set. The heat relaxation as disclosed by Lennard is performed by placing the filament on a rack in an annealing oven and allowing the filament to shrink from about 16 to about 35 percent of the original length of the filament. The annealing is carried out at a temperature within the range of from about 135° C. to about 152° C., for a period of time sufficient to permit the filament to shrink and heat set normally 5 to about 40 minutes.

As good as the fibers are that may be produced from the processes disclosed by Listner and Lennard there is room for improvement in these processes. In particular it would be desirable to eliminate the separate annealing step performed on the filaments after the filament has been draw to stream line the suture product and handling.

Thus it is an object of the present invention to provide a process for producing polypropylene suture that eliminates the rack annealing of polypropylene sutures. This and other objects and advantages of the present invention will be obvious to those skilled in the art from the following specification.

SUMMARY OF THE INVENTION

We have discovered a process for producing a polypropylene suture comprising the steps of (a) extruding melted polypropylene resin through an orifice and rapidly quenching the melted polypropylene resin to produce a filament; (b) drawing the filament in the range of from about 4× to about 7.5× in a first drawing zone to produce a drawn filament; (c) drawing the singly drawn filament in a second drawing zone in the range of from about 1.0× to about 2.5× while in a first heated zone being maintained at a temperature in the range of from about 30° C. to about 160° C., to form a doubly drawn filament; (d) relaxing the doubly drawn filament in the range of from about 0.75× to about 0.95×, in a second heated zone being maintained at a temperature in the range of from about 100° C. to about 180° C., to form a polypropylene suture.

BRIEF DESCRIPTION OF THE FIGURES

The FIGURE is a side elevation, partially schematic of an apparatus suitable for carrying out the process of the present invention.

DETAILED DESCRIPTION OF THE INVENTION

As used herein the term polypropylene shall include isotactic and syndiotactic polypropylene and blends thereof, as well as, blends composed predominantly of isotactic or syndiotactic polypropylene blended with heterotactic polypropylene and polyethylene (such as is described in U.S. Pat. No. 4,557,264 issued Dec. 10, 1985 assigned to Ethicon, Inc. hereby incorporated by reference) and copolymers composed predominantly of propylene and other alpha-olefins such as ethylene (which is described in U.S. Pat. No. 4,520,822 issued Jun. 4, 1985 assigned to Ethicon, hereby incorporated by reference). The preferred method for preparing the flexible polypropylene sutures of the present invention utilizes as the raw material pellets of isotactic polypropylene homopolymer having a weight average molecular weight of from about 260,00 to about 420,000. Polypropylene of the desired grade is commercially available in both powder and pellet form.

Referring to the FIGURE, there is shown an apparatus that is suitable for carrying out the present invention. An extruder 10 is terminated at one end with an extrusion die 12. A longitudinal extruder screw is mounted for rotation within the barrel 16 and is driven by a variable speed motor 18 through a gear 20. Polypropylene pellets are introduced into the extruder through hopper 22 which communicates with the barrel 16. In normal operation of the extruder 10, the feeding zone 24 of the extruder is maintained at a temperature in the range of from about 140° C. to about 200° C., the transition zone 26 is maintained at a temperature in the range of from about 170° C. to about 220° C., and the pump block 30, block 28 and die 12 are maintained at a temperature in the range of from about 170° C. to about 225° C. A pump 33 driven by a motor 32, pumps the molten polypropylene through spinneret orifices in the die 12 to form a plurality of filaments 31 (for simplicity only one filament is shown in the FIGURE). The filament 31 is extruded into quench bath 34. The quench bath 34 is filled with a liquid heat exchange medium. The surface of the liquid in the quench bath 34 is preferably not more than a few centimeter below the die 12 in order to achieve rapid cooling of the extruded filament 31. The quench bath 34 is maintained at a temperature below 50° C. and preferably the quench bath 34 is maintained at about room temperature. The filament 31 enters the quench bath 34 and travels around idler roll 36 in the quench bath 34 and then up out of the quench bath 34 to another idle roller 35 then to the first godet 37 in the first drawing zone 2. In the first drawing zone 2 the filament 31 is drawn in the range of from about 5× to 7.5× its original length. The filament 31 may be drawn incrementally or in several discrete steps in the first drawing zone 2. The drawing will preferably be performed in a first heated zone 41 (such as a heated cabinet, oven, or by using heated godets). The temperature of the first heated zone will preferably be in the range of from about 30° C. to about 170° C. Most preferably the first and second godet will be maintained at a temperature in the range of from about 40° C. to 140° C. The filament 31 will remain in the first heated zone 41 generally only a short time preferably in the range of from about 0.1 seconds to about 10 seconds.

In the preferred embodiment of the invention shown in the attached FIGURE, the filament 31 is drawn by a first godet 37 and a second godet 42. The first godet 37 includes a main roll 38 and an air bearing 40. The first godet 37 is rotated at a peripheral speed that is equal to or slightly higher than the speed at which the filament 31 is extruded from the die orifice 12. The first godet 37 may be combined with a pinch roller (not shown) to assure the filament 31 does not slip in the subsequent drawing to the extruded filament 31. The first draw of the extruded filament 31 will be performed by feeding the extruded filament 31 from the first godet 37 to second godet 42 which includes a main roll 43 and an air bearing 44. The second godet 42 is rotated at a peripheral speed that is in the range of from about 5× to about 7.5× of the speed of the first godet 37.

The filament 31 then passes into a second drawing zone 4, where the filament 31 is drawn again in the range of from about 1.0× to about 2.5× while in a second heated zone 46. The filament 31 may be drawn incrementally or in one or more discrete steps in the second drawing zone 4. The drawing will be performed in a second heated zone 46. The temperature of the second heated zone 46 will be in the range of from about 30° C. to about 180° C., preferably in the range of from about 75° C. to about 140° C. The filament 31 will remain in the second heated zone 46 generally only a short time preferably in the range of from about 0.1 seconds to about 10 seconds.

In the preferred embodiment of the invention shown in the attached FIGURE, the filament 31 passes through a second heated zone 46 to a third godet 50. The second heated zone 46 is preferably an orienting oven 48 that is maintained at a temperature of in the range of from about 30° C. to about 180° C., preferably in the range of from about 75° C. to about 140° C. and most preferably in the range of from 120° C. to about 140° C. The filament 31 is drawn in the range of from about 1× to about 2×, while traveling from the second godet 42 to the third godet 50 in the second heated zone 46. The third godet 50 includes a main roll 51 and an air bearing 52, that are rotating at a peripheral speed of about 1× to about 2.5× of the peripheral speed of the second godet 42. Preferably the draw ratio will be in the range of from about 1.06× to about 1.9×.

The filament 31 then passes from the second drawing zone 4 into an annealing zone 6, where the filament 31 is annealed and allowed to shrink. In the annealing zone 6 the filament 31 is placed in a third heated zone 54 that is maintained at a temperature in the range of from about 100° C. to about 180° C. wherein the filament is allowed to shrink in the range of about 5 percent to about 35 percent and preferably from about 5 to about 25 percent of the filament original length. The filament 31 may be allowed to shrink incrementally or in one or more discrete steps in the third heated zone 54. The filament 31 will remain in the third heated zone 54 for a short time generally in the range of from about 0.1 to about 20 seconds and preferably in the range of from about 0.1 seconds to 5 seconds.

In the preferred embodiment of the present invention shown in the attached FIGURE, the filament 31 then passes through a third heated zone 54 to a fourth godet 56. The heated zone 54 is preferably an annealing oven 60, that is maintained at a temperature of in the range of from about 100° C. to 180° C. The filament 31 is then allowed to shrink in the range of from about 75 percent to about 95 percent of its original length. The fourth godet 56 includes a main roll 57 and an air bearing 58, that are rotating at a peripheral speed of about 0.75× to about 0.95× of the peripheral speed of the third godet 50. Preferably the relaxation ratio will be in the range of from about 0.8× to about 0.9×. After passing around the fourth godet 56, the filament 31 may then be fabricated into sutures.

The overall draw ratio, that is, the difference between the peripheral speed of the fourth godet 56 and the first godet 37, will ordinarily be from about 6× to about 8× and preferably the total draw ratio will be in the range of from about 6.4× to about 6.7×.

The residence time of filament 31 within any of the heated zones can be optimized to improve fiber properties. The overall residence time that filament 31 is present in the second and third heated zones will preferably be in the range of from about 2 seconds to about 50 seconds and most preferably in the range of from about 4 seconds to about 20 seconds. The residence time can be increased with longer ovens or by having multiple wraps of the fiber in the oven.

The filaments of the present invention may be fabricated into surgical sutures in accordance with customary procedures without additional annealing. The filaments coming off the fourth godet 56 may be inspected and cut to length using an in-line cutting device. In a fully automated line the cut lengths of suture would then be swaged. One suitable device for automatically cutting and swaging is disclosed in copending U.S. patent application Ser. No. 181,606 filed Jan. 13, 1994, assigned to Ethicon, Inc., which is incorporated herein by reference. Alternatively for convenience the filament 31 coming off the fourth godet 56 may proceed to a windup station 62 and be wound onto spools 70 for later use. The filament 31 may be stored before further processing to allow the filament 31 to achieve complete stability of all its properties such as modulus (which may continue to rise for 18 to 120 hours after manufacture). Those skilled in the art can readily determine if any optimum storage time exist before further processing.

If the filament 31 is stored on spools 70 the filament 31 may acquire a tendency to bend or curl in a circular pattern commonly referred to as a filament memory. To facilitate further processing of the filament 31 it may be desirable to expose the filament to a fourth heated zone to remove the memory as the filament 31 is further handled and inspected. In one embodiment of the present invention the filament 31 would be removed from the spool 70 and exposed to the fourth heated zone maintained at a temperature in the range of from about 50° C. to about 80° C. The filament 31 would be exposed to the fourth heated zone 72 for a very short period of time preferably in the range of from about 24 hours to about 2 hours. In the fourth heated zone because of the low temperature and short time of exposure of the filament 31 to the temperature no appreciable shrinkage of the filament 31 should occur.

The following non-limiting examples are further provided to illustrate the practice of the present invention.

EXAMPLE

Dyed isotactic polypropylene having a melt flow of 3–5 as determined by ASTM D1238 was used to produce surgical sutures under the conditions set forth in Table 1 below.

TABLE 1

| Sample No. | 1 | 2 | 3 | 4 | 5 |
|---|---|---|---|---|---|
| Filament Size | 2 | 2 | 2/0 | 6/0 | 6/0 |
| Feed Zone °F. | 320 | 320 | 320 | 320 | 320 |
| Transition Zone °F. | 366 | 366 | 365 | 365 | 365 |
| Pump °F. | 365 | 366 | 365 | 391 | 390 |
| Block °F. | 375 | 375 | 370 | 400 | 400 |
| Die °F. | 375 | 375 | 375 | 400 | 400 |
| Barrel PSI | 1501 | 1506 | 1501 | 1505 | 1506 |
| Pump PSI | 1286 | 1277 | 828 | 657 | 647 |
| Die PSI | 183 | 191 | 412 | 161 | 162 |
| Pump RPM | 11.2 | 24[1] | 6.1 | 4.8 | 4.8 |
| Screw RPM | 24.6 | 11.1[1] | 13.9 | 5 | 5 |
| Godet 1 FPM/°F. | 10/270 | 10/270 | 14.7/246 | 19/130 | 19/130 |
| Godet 2 FPM/°F. | 72/185 | 72/185 | 103/180 | 105/190 | 105/190 |
| Orienting Oven °F. | 315 | 265 | 295 | 265 | 212 |
| Godet 3 FPM/°F. | 76/170 | 76/170 | 117/190 | 147/170 | 147 |
| Annealing Oven °F. | 265 | — | 270 | 212 | — |
| Godet 4 FPM/°F. | 64 | — | 97 | 127 | — |

RPM is revolutions perminute.
FPM is feet per minute.
[1]The original data page appears to have reversed these numbers.

The surgical sutures 2 and 5 were wound on racks and annealed for 10–20 minutes in an annealing oven at 129°–145° C. All the samples were sterilized and tested using the following test procedures. The data from these test are presented in Table 2.

The characteristic properties of the sutures samples 1–6 were determined by conventional test procedures. The tensile properties (i.e., straight and knot tensile strengths and elongation) displayed herein were determined with an INSTRON Tensile Tester. The settings used to determine the straight tensile, knot tensile and break elongation were the following, unless indicated:

TABLE 2

|  | GAUGE LENGTH (cm) | CHART SPEED (cm) | CROSSHEAD SPEED (cm/min.) |
|---|---|---|---|
| STRAIGHT TENSILE | 12.7 | 30.5 | 30.5 |
| KNOT TENSILE | 12.7 | 30.5 | 30.5 |
| BREAK ELONGATION | 12.7 | 30.5 | 30.5 |

The straight tensile strength was calculated by dividing the force to break by the initial cross-sectional area of the suture. The elongation at break was read directly from the stress-strain curve of the sample.

The knot tensile strength of a suture was determined in separate tests. The surgeon's knot was a square knot in which the free end was first passed twice, instead of once, through the loop, and the ends drawn taut so that a single knot was superimposed upon a compound knot. The first knot was started with the left end over the right end and sufficient tension was exerted to tie the knot securely.

The specimen was placed in the INSTRON Tensile Tester with the knot approximately midway between the clamps. The knot tensile strength was calculated by dividing the force required to break by the initial cross-sectional area of the fiber. The tensile strength values are reported in KPSI ($PSI \times 10^3$).

TABLE 3

Comparison of In-line and Rack Annealed Properties

| Sample No. | Size | Diameter (mils) | Tensile lbs. | Strength psi | Knot. lbs | Strength psi | Elongation % | Modulus kpsi |
|---|---|---|---|---|---|---|---|---|
| 1 | 2 | 21.35 | 20.46 | 57150.00 | 13.36 | 37490.00 | 33.47 | 380.40 |
| 2 | 2 | 21.42 | 20.58 | 57080.00 | 12.98 | 36080.00 | 33.67 | 340.90 |
| 3 | 2/0 | 12.68 | 8.46 | 68060.00 | 6.45 | 51760.00 | 40.28 | 283.10 |
| 4 | 6/0 | 3.60 | 1.08 | 105800.00 | 0.74 | 72320.00 | 24.15 | 629.70 |
| 5 | 6/0 | 3.62 | 1.05 | 102100.00 | 0.78 | 76240.00 | 32.51 | 422.00 |

Sample Numbers 1, 3 and 4 were produced by the inventive in-line annealing process described above. Samples 2 and 5 were produced by rack annealing the sutures following conventional manufacturing procedures. The data above demonstrates that the inventive process produces sutures that have suitable properties for being used as sutures.

We claim:

1. An in-line process for producing a polypropylene suture comprising performing the steps of (a) extruding melted polypropylene resin through an orifice and rapidly quenching the melted polypropylene resin to produce a filament; (b) drawing the filament in the range of from about 4× to about 7.5× in a first drawing zone to produce a drawn filament; (c) drawing the singly drawn filament in a second drawing zone in the range of from about 1.0× to about 2.5× while in a second heated zone being maintained at a temperature in the range of from about 30° C. to about 160° C., to form a doubly drawn filament; (d) relaxing and annealing the doubly drawn filament in the range of from about 0.75× to about 0.9×, in a third heated zone being maintained at a temperature in the range of from about 100° C. to about 180° C., to form an annealed polypropylene suture.

2. The process of claim 1 wherein the filament in the first drawing zone is exposed to a first heated zone being maintained at a temperature in the range of from about 30° C. to about 170° C.

3. The process of claim 1 wherein the filament is drawn in a single step in the first draw zone.

4. The process of claim 3 wherein the filament is drawn by a first and a second heated godets.

5. The process of claim 2 wherein the second heated zone is maintained at a temperature in the range of from about 75° C. to about 140° C.

6. The process of claim 2 wherein the singly drawn filament is drawn in the range of from about 1.06× to about 1.9× the second drawing zone.

7. An in-line process for producing a polypropylene suture comprising the steps of (a) extruding melted polypropylene resin through an orifice and rapidly quenching the melted polypropylene resin to produce a filament; (b) drawing the filament in the range of from about 4× to about 7.5× in a first drawing zone while in a first heated zone being maintained at a temperature in the range of from about 40° C. to about 140° C., to produce a drawn filament; (c) drawing the drawn filament in a second drawing zone in the range of from about 1.0× to about 1.9× while in a second heated zone being maintained at a temperature in the range of from about 75° C. to about 140° C., to form a doubly drawn filament; (d) relaxing and annealing the doubly drawn filament in the range of from about 0.80× to about 0.9×, in a third heated zone being maintained at a temperature in the range of from about 100° C. to about 180° C., to form an annealed polypropylene suture.

8. The process of claim 7 wherein the total draw ratio of the suture from drawing and relaxing is in the range of from about 6 to about 8.

9. The process of claim 1 wherein the doubly drawn filament is relaxed in the range of from about 0.8× to about 0.9×.

* * * * *